(12) United States Patent
Vetter

(10) Patent No.: US 8,947,358 B2
(45) Date of Patent: Feb. 3, 2015

(54) PERSONAL CARE APPLIANCE KIT

(71) Applicant: Braun GmbH (a German Corporation), Kronberg (DE)

(72) Inventor: Ingo Vetter, Karben (DE)

(73) Assignee: Braun GmbH, Kronberg (DE)

( * ) Notice: Subject to any disclaimer, the term of this patent is extended or adjusted under 35 U.S.C. 154(b) by 193 days.

(21) Appl. No.: 13/743,361

(22) Filed: Jan. 17, 2013

(65) Prior Publication Data

US 2013/0188112 A1    Jul. 25, 2013

(30) Foreign Application Priority Data

Jan. 20, 2012  (EP) .................................. 12152012

(51) Int. Cl.

| G02F 1/1333 | (2006.01) |
|---|---|
| G02F 1/1335 | (2006.01) |
| G09G 5/00 | (2006.01) |
| G06F 3/033 | (2013.01) |
| G09G 5/08 | (2006.01) |
| H04N 5/64 | (2006.01) |
| H04N 21/422 | (2011.01) |
| G02F 1/13 | (2006.01) |
| A46B 15/00 | (2006.01) |
| A61C 17/16 | (2006.01) |
| A45D 26/00 | (2006.01) |

(52) U.S. Cl.
CPC ............ G02F 1/133308 (2013.01); H04N 5/64 (2013.01); H04N 21/4222 (2013.01); G02F 1/1313 (2013.01); A46B 15/0038 (2013.01); A61C 17/16 (2013.01); A46B 2200/1066 (2013.01); A45D 2026/008 (2013.01)
USPC ............... 345/158; 349/58; 349/96; 345/156; 15/167.1

(58) Field of Classification Search
CPC .... H04N 5/64; A46B 13/02; G02F 1/133308; G02F 1/1313
USPC ............... 345/156, 158; 349/58, 96; 15/167.1
See application file for complete search history.

(56) References Cited

U.S. PATENT DOCUMENTS

| 2004/0239619 A1* | 12/2004 | Takahashi et al. ............ 345/156 |
|---|---|---|
| 2008/0103267 A1 | 5/2008 | Hurst et al. |
| 2008/0141478 A1* | 6/2008 | Gatzemeyer et al. ........ 15/167.1 |

FOREIGN PATENT DOCUMENTS

| JP | 2006 1557702 A | 6/2006 |
|---|---|---|
| KR | 2009 0033951 A | 4/2009 |
| WO | WO 2007/091130 A1 | 8/2007 |

OTHER PUBLICATIONS

European Search Report for EP 12 15 2012 dated Jul. 27, 2012.

*Primary Examiner* — Nathanael R Briggs
(74) *Attorney, Agent, or Firm* — Vladimir Vitenberg

(57) ABSTRACT

The personal care appliance kit includes a display device; and a handle for an electric device. The display device includes a continuous front panel; a window area being a part of the front panel, which window area is transmissible with respect to an infrared signal radiation; a display area being a part of the front panel, which display area is less transmissible than the window area with respect to the infrared signal radiation; and a receiver unit placed on a backside of the window area and adapted for receiving the infrared signal radiation from a transmitter unit for emitting the infrared signal radiation of the handle for indicating a handle use status; wherein the front panel is a liquid crystal display panel having at least one polarization filter layer; and wherein the at least one polarization filter layer is provided with a cut-out in the window area.

10 Claims, 2 Drawing Sheets

PERSONAL CARE APPLIANCE KIT

FIELD OF THE INVENTION

The present disclosure is directed to a personal care appliance kit comprising a display device and a handle for a personal care appliance. More particularly, the present disclosure is directed to a personal care appliance kit comprising a display device having a receiver unit and one of an oral care handle or shaver handle or epilator handle.

BACKGROUND OF THE INVENTION

It is known that certain display devices such as flat display devices, e.g. flat TV devices, are equipped with a receiver window that is transmissible with respect to infrared (IR) radiation. The IR window is typically placed in the housing of the display device.

It is also known to provide display devices that are intended for use in a wet or at least humid environment such as the bathroom and thus need to fulfill high standards with respect to water tightness.

There is however, a need for a personal care appliance kit comprising a display device and a handle for a personal care appliance such that the display device is in particular suitable for use in a wet or humid environment.

SUMMARY OF THE INVENTION

In one embodiment, a personal care appliance kit is provided. The personal care appliance kit includes a display device; and a handle for an electric device. The display device includes a continuous front panel; a window area being a part of the front panel, which window area is transmissible with respect to an infrared signal radiation; a display area being a part of the front panel, which display area is less transmissible than the window area with respect to the infrared signal radiation; and a receiver unit placed on a backside of the window area and adapted for receiving the infrared signal radiation from a transmitter unit for emitting the infrared signal radiation of the handle for indicating a handle use status; wherein the front panel is a liquid crystal display panel having at least one polarization filter layer; and wherein the at least one polarization filter layer is provided with a cut-out in the window area.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

Figure 1:
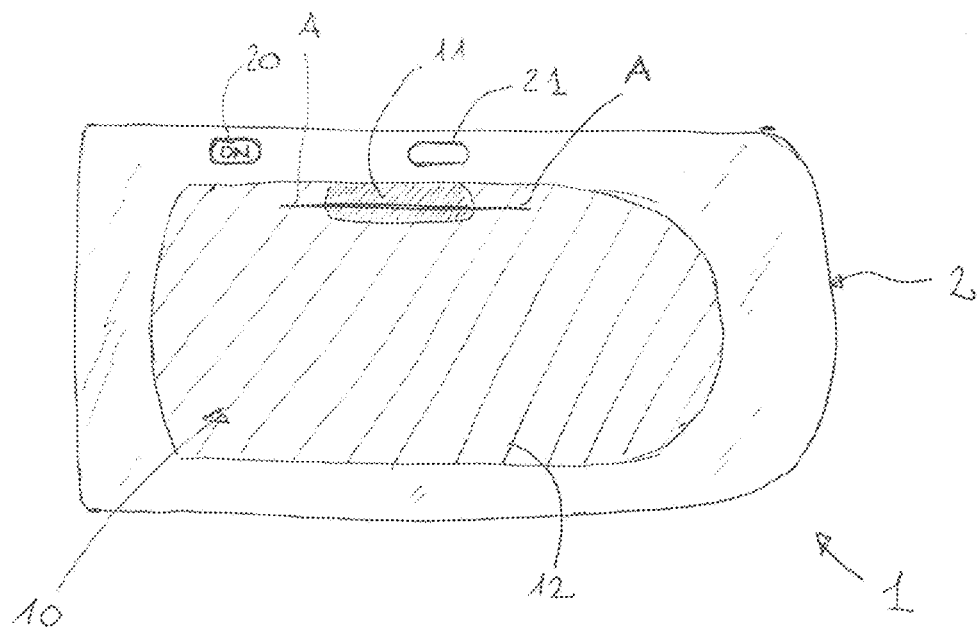
FIG. 1 is a schematic depiction of a display device of a personal appliance kit according to embodiments shown and described herein.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to the present disclosure, a personal care appliance kit is provided. In one embodiment, the kit includes a display device that has a continuous front panel, a window area being a part of the front panel, which window area is transmissible with respect to a signal radiation, a display area being a part of the front panel, which display area is less transmissible with respect to the signal radiation, and a receiver unit placed on a backside of the window area and adapted for receiving the signal radiation. Thus, a display device is provided that does not require a further signal radiation receiver window and further the device can be made water proof by mounting only the front panel in a water-tight manner. In some embodiments, the front panel is mounted in the display device in a water-proof manner. In the context of the present disclosure, "backside" means the side opposite to the side intended for being visible by the viewer or, in other words, the side opposite to the side onto which the signal radiation impinges during operation.

In the context of the present disclosure, "transmissible" with respect to the signal radiation means that the window area allows transmission of signal radiation in an amount that the receiver unit can reliably detect signals conveyed by the signal radiation when the signal radiation has an intensity value above a certain signal radiation threshold level and is impinging onto the window area. In contrast, the display area is less transmissible to the signal radiation and thus may not allow for reliably detecting presence of the signal radiation having an intensity value above the signal radiation threshold level and impinging onto the display area by a receiver unit placed behind the display area. In some embodiments, the signal intensity of the signal radiation after it has passed the window area is about 25% higher than the signal intensity of the signal radiation after it has passed the display area (i.e. the signal ratio between the signal intensity in the window area and the signal intensity in the display area is at least about 1.25). In some embodiments, the signal ratio is about 1.5, 2, 2.5, 3, 3.5, 4, 4.5, 5, 6, 7, 8, 9, or 10 or higher.

In some embodiments, the front panel may be realized as a liquid crystal display (LCD) panel having at least one polarization filter that to a certain extent absorbs the signal radiation and wherein the polarization layer does not extend into the window area, i.e. the polarization filter may have a cut-out determining the window area. In some embodiments, a liquid crystal layer of the LCD does not extend into the window area. In some embodiments, the display area is at least essentially non-transmissible with respect to the signal radiation, where "essentially non-transmissible" here means that less than 10% of the impinging signal radiation transmits the display area without being absorbed.

In some embodiments, the window area is located at a border of the front panel. In some other embodiments, the window area may be located in a more central area of the front panel, in particular in case that the front panel area comprises areas where no information should be displayed, which areas could then be used to locate the window area. Generally, in some embodiments, the window area may have a surface size between about 1 mm$^2$ and about 1000 mm$^2$, in another embodiment between about 10 mm$^2$ and about 100 mm$^2$, and in yet another embodiment between about 20 mm$^2$ and about 60 mm$^2$. In some embodiments, the display area has a surface size of between about 200 mm$^2$ and about 50,000 mm$^2$. In some embodiments, the surface size of the window area is less than about 10% of the surface size of the display area, in particular less than about 9%, 8%, 7%, 6%, 5%, 4%, 3%, 2%, or 1%.

In some embodiments, the signal radiation may be infrared radiation, for example, near infrared radiation, but this should not be interpreted as limiting. Other radiation types could also be used as signal radiation, for example, ultraviolet radiation, visible radiation or radio frequency radiation. In some embodiments, the receiver unit and a control circuitry for controlling the display area are arranged on a single circuitry board.

In accordance with at least one aspect, a kit is provided that comprises a display device as proposed and an electric device that comprises a transmitter unit for transmitting the signal radiation. In some embodiments, the transmitter unit may have receiving functionality, i.e. may be realized as a transceiver unit. In some other embodiments, an additional receiver unit is arranged in the electric device. The electric device may be an oral hygiene device such as an electric or manually operated toothbrush, an electric flossing device, an interdental cleaner, a gum massaging device etc. or as a personal grooming device such as an electric shaver or a manually operated razor, an epilator, a skin massaging device etc. The electric device may be equipped to transmit certain information to the display device using a wireless transmission technology on basis of the signal radiation. Such information may range from simple information such as indicating the switching on/off of the electric device, the time of usage etc. to more complex information such as a life image of the area that is treated by the electric device, for example, a life skin image.

While the embodiments discussed with respect to the figures focus on a display device where the front panel is realized as a LCD panel, this should not be interpreted as limiting and other front panels could also be used such as an electronic ink panel or an organic light emitting diode (OLED) panel. An LCD panel may be realized as an active matrix display comprising a matrix of thin film transistors (TFT) and/or with light emitting diode (LED) backlighting etc.

Features discussed in accordance with a particular embodiment shall be considered as individually disclosed and thus combinable with all other features described in the present application to the extent that such combination is technically possible and not explicitly excluded.

FIG. 1 is a schematic depiction of an example embodiment of a display device 1 as proposed. The display device has a front panel 10 that may be mounted into a housing 2. In some embodiments, the front panel 10 is mounted into the housing 2 in a water tight manner such that during use of the display device 1 in a wet or humid environment penetration of liquids, such as water, or humidity into the device is at least partly inhibited and the interior of the display device 1 is thus better protected from damages originating from liquids or humidity. The front panel 10 has a window area 11 and a display area 12. The display area 12 is intended for displaying of information. In accordance with the present disclosure, the display area 12 is less transmissible with respect to a signal radiation than the window area 11. In some embodiments, the display area may be essentially non-transmissible with respect to the signal radiation.

In some embodiments, the display device 1 may comprise interaction elements 20, 21 such as push buttons, capacitive switches etc. in order to switch the display device 1 on or off or to set parameters of the display device 1 etc. Instead of being arranged on the housing front, the interaction elements may be arranged under a water tight protection cover that may be detachable for using the interaction elements.

In some embodiments, the front panel may be a liquid crystal display (LCD) panel, as will be explained in more detail with respect to FIG. 2. In some embodiments, the signal radiation may be infrared radtion, in other embodiments the signal radiation may be radio frequency radiation.

Figure 2:
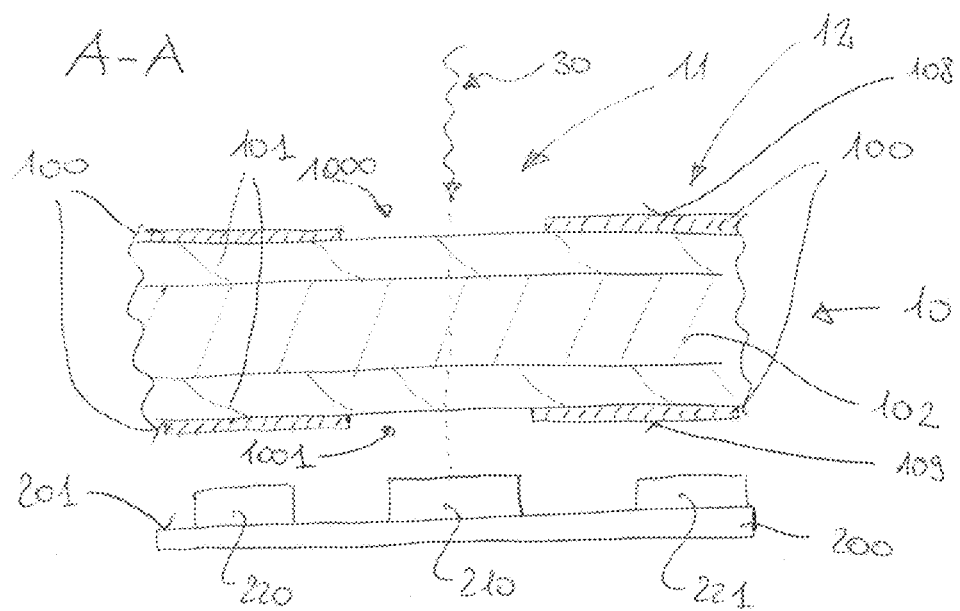
FIG. 2 is a schematic cross sectional cut through the display device of FIG. 1.

FIG. 2 is a schematic cross sectional cut through a part of an example embodiment of a display device and may be taken along line A-A shown in FIG. 1. This cross sectional cut is used for illustration of some features of an example embodiment of a display device as proposed and shall not be interpreted as being complete. FIG. 2 shows a cut through a part of a front panel 10 that may be a liquid crystal display (LCD) panel. Only some aspects of a LCD are shown as the general structure of a LCD panel is known to the skilled person. The front panel 10 comprises several layers. A liquid crystal layer 102 is sandwiched between two glass substrates 101 and on each one of the glass substrates 101 a polarization layer 100 is provided on an outer surface (i.e. the surface distal to the liquid crystal layer 102) of the respective glass substrate 100. The polarization layers 100 strongly absorb, for example, infrared radiation that may be used as signal radiation. In FIG. 2, the polarization layers 100 have cut-outs 1000 and 1001, respectively, which are in alignment in size and shape with each other with respect to a perpendicular axis that crosses the front panel 10 at 90 degrees. In some embodiments, an alignment in size and/or shape is not required as long as there is an overlap between the upper and the lower cut-outs such that signal radiation (indicated by wavy line and arrow 30 in FIG. 2) impinging vertically onto the front panel 10 could penetrate through the front panel without crossing a polarization layer 100. The area where the cut-outs of the polarization layer are in alignment determine the window area 11. In some embodiments, only a single polarization layer is provided and then the respective cut-out determines the window area. The remaining area of the front panel represents the display area 12. It is schematically shown in FIG. 2 that a circuitry board 200 is arranged underneath the front panel (where "underneath" means inside of the housing (shown in FIG. 1) of the display device, i.e. opposite to the front side 108 of the front panel 10). The circuitry board 200 has a mounting side 201 that faces the backside 109 of the front panel 10. A receiver unit 210 is mounted on the mounting side 201 of the circuitry board 200 at a location that is in alignment with the window area 11 with respect to a vertical axis though the front panel 10 (indicated by a dotted line in FIG. 2). The receiving unit 210 may be adapted for receiving the signal radiation 30 and for generating an output signal that may be proportional to the intensity of signal radiation 30 or that may be positive when the signal radiation intensity is above a predetermined threshold and zero when the signal radiation intensity is below the threshold value. The receiver unit may in particular be adapted to reliably output a detection signal when the intensity value of the signal radiation impinging vertically onto the front side of the front panel is above a signal radiation threshold value. Further circuitry components 220, 221 may be mounted on the circuitry board 200. These further circuitry components 220, 221 may for example be control circuitry components for controlling the display of information on the display area 12 of the front panel 10.

In another embodiment, the signal radiation is radio frequency radiation and the window area is then a part of the front panel that is kept free of any conductive layers that would absorb radio frequency radiation.

Figure 3:
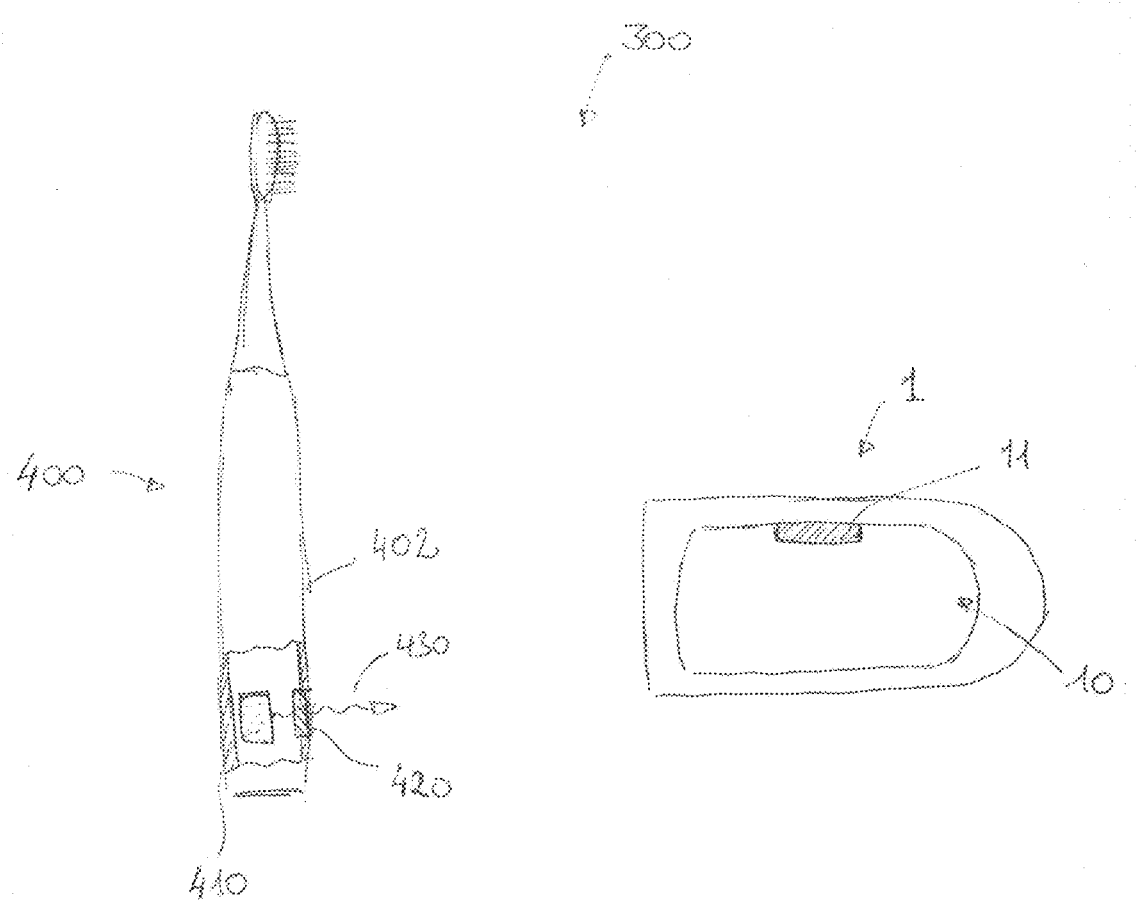
FIG. 3 is a schematic depiction of a kit comprising a display device and an electric device according to embodiments shown and described herein.

FIG. 3 is a depiction of a kit comprising a display device 1 as proposed in the present disclosure and an electric device 400 that in particular can be held in a user's hand. In one embodiment, the electric device 400 may be an oral hygiene device such as a toothbrush (as shown in FIG. 3) or a personal grooming device such as an electric shaver. The display device has a front panel 10 and the front panel comprises a window area 11 that is tranmissive with respect to a signal radiation. The electric device 400 may have a transmitter unit 410 for emitting the signal radiation 430. The electric device 400 may further have a housing 402 comprising a signal radiation window 420 that is transmissible with respect to the signal radiation 430 such that the signal radiation can exit the electric device 400. The signal radiation window 420 may in particular be placed such that it is located on the side of the electric device 400 that faces outwards from the user when the electric device 400 is held by the user during operation. The signal radiation emitted by the transmitter unit 410 can then conveniently reach the display device 1 that may be placed on a shelf or the like in the bathroom, for example, under the mirror. In some embodiments, the electric device may be equipped with a transceiver unit instead of a transmitter unit so that it can also receive signal radiation or the electric device may additionally be equipped with a receiver unit for receiving signal radiation. In an embodiment with a transceiver unit or an additional receiver unit, these units may be arranged to receive a signal radiation that is different to the signal radiation that the receiver unit in the display device, e.g. the receiver unit in the display device may be equipped to receive infrared radiation while the receiver unit/transceiver unit in the electric device may be quipped to receive radio frequency radiation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A personal care appliance kit comprising:
   a display device; and
   a handle for an electric device;
   wherein the display device includes a continuous front panel; a window area being a part of the front panel, which window area is transmissible with respect to an infrared signal radiation; a display area being a part of the front panel, which display area is less transmissible than the window area with respect to the infrared signal radiation; and a receiver unit placed on a backside of the window area and adapted for receiving the infrared signal radiation from a transmitter unit for emitting the infrared signal radiation of the handle for indicating a handle use status; wherein the front panel is a liquid crystal display panel having at least one polarization filter layer; and wherein the at least one polarization filter layer is provided with a cut-out in the window area.

2. The personal care appliance kit according to claim 1, wherein the ratio between the signal intensity of the signal radiation after having passed through the window area and of the signal intensity of the signal radiation after having passed through the display area is at least about 1.25 or higher.

3. The personal care appliance kit according to claim 2, wherein a liquid crystal layer of the liquid crystal display panel does not extend into the window area.

4. The personal care appliance kit according to claim 1, wherein the window area is located at a border of the front panel.

5. The personal care appliance kit according to claim 1, wherein the receiver unit and a control circuitry for controlling the display area are arranged on a single circuitry board.

6. The personal care appliance kit according to claim 1, wherein the window area has a size of between about 1 mm$^2$ to about 1000 mm$^2$.

7. The personal care appliance kit according to claim 1, wherein the front panel is mounted into a housing of the display device.

8. The personal care appliance kit according to claim 1, wherein the window area is structured such that it allows reliable detection of a signal conveyed by the signal radiation by the receiver unit when the signal radiation has an intensity value at the window area entrance side of above a signal radiation threshold value and is impinging essentially perpendicularly onto the window area and wherein the display area is structured to be less transmissible such that it would not allow reliable detection of the signal by the receiver unit.

9. The personal care appliance kit according to claim 8, wherein the receiver unit is arranged such that is allows for reliably detecting a signal conveyed by the signal radiation when the intensity value of the signal radiation impinging onto the window area is above the signal radiation threshold value.

10. The personal care appliance kit according to claim 1, wherein the electric device is selected from the group consisting of a toothbrush, a flosser, an interdental cleaner, a gum massager, a shaver, a razor, an epilator and a skin massager.

* * * * *